United States Patent
Takahashi et al.

(10) Patent No.: US 10,932,652 B2
(45) Date of Patent: Mar. 2, 2021

(54) ENDOSCOPE, IMAGE PICKUP UNIT, AND METHOD OF REPLACING IMAGE PICKUP DEVICE IN ENDOSCOPE

(71) Applicant: OLYMPUS CORPORATION, Tokyo (JP)

(72) Inventors: Masafumi Takahashi, Hino (JP); Atsushi Goto, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/788,436

(22) Filed: Feb. 12, 2020

(65) Prior Publication Data

US 2020/0297193 A1     Sep. 24, 2020

Related U.S. Application Data

(63) Continuation of application No. PCT/JP2018/018804, filed on May 15, 2018.

(30) Foreign Application Priority Data

Aug. 29, 2017   (JP) ............................. JP2017-164705

(51) Int. Cl.
*A61B 1/00* (2006.01)
*A61B 1/05* (2006.01)
(Continued)

(52) U.S. Cl.
CPC ...... *A61B 1/00105* (2013.01); *A61B 1/00096* (2013.01); *A61B 1/051* (2013.01);
(Continued)

(58) Field of Classification Search
None
See application file for complete search history.

(56) References Cited

U.S. PATENT DOCUMENTS

2007/0118019 A1   5/2007   Mitani et al.
2010/0288524 A1*  11/2010  Tagawa ................ H01J 31/127
                                                    174/50.5
2014/0320617 A1*  10/2014  Parks ................. A61B 1/00181
                                                    348/65

FOREIGN PATENT DOCUMENTS

JP     H0621252 A      1/1994
JP     2001-128930 A   5/2001
(Continued)

OTHER PUBLICATIONS

International Search Report dated on Jul. 31, 2018 issued in PCT/JP2018/018804.

*Primary Examiner* — Stuart D Bennett
(74) *Attorney, Agent, or Firm* — Scully, Scott, Murphy & Presser, P.C.

(57) ABSTRACT

An endoscope includes an image pickup device inserted into a through hole in a housing, in which the image pickup device includes an optical unit including a distal end lens and optical members, and an image pickup unit, the distal end lens is fixed to a distal end portion of the through hole, the optical members are held by a lens frame, the lens frame being inserted into the through hole, and a part of the lens frame being bonded to the through hole, and the image pickup unit includes a unit frame fixed to the lens frame, a front portion of the unit frame being inserted into the through hole and being bonded to the through hole, and an outer surface of a rear portion of the unit frame including stoppers to which a jig is to be fixed, the rear portion not being inserted into the through hole.

6 Claims, 4 Drawing Sheets

(51) Int. Cl.
*G02B 7/02* (2021.01)
*H04N 5/225* (2006.01)
*H04N 7/18* (2006.01)

(52) U.S. Cl.
CPC .......... *G02B 7/021* (2013.01); *H04N 5/2253* (2013.01); *H04N 5/2254* (2013.01); *H04N 7/18* (2013.01); *H04N 2005/2255* (2013.01)

(56) References Cited

FOREIGN PATENT DOCUMENTS

| | | | |
|---|---|---|---|
| JP | 2005-227728 A | | 8/2005 |
| JP | 2005-287633 A | | 10/2005 |
| JP | 2005287633 A | * | 10/2005 |
| JP | 2006-015076 A | | 1/2006 |
| JP | 2006-075446 A | | 3/2006 |
| JP | 2008-200158 A | | 9/2008 |
| JP | 2008200158 A | * | 9/2008 |
| JP | 2010-267541 A | | 11/2010 |
| WO | WO2006/004123 A1 | | 1/2006 |

\* cited by examiner

ENDOSCOPE, IMAGE PICKUP UNIT, AND METHOD OF REPLACING IMAGE PICKUP DEVICE IN ENDOSCOPE

CROSS REFERENCE TO RELATED APPLICATION

This application is a continuation application of PCT/JP2018/018804 filed on May 15, 2018 and claims benefit of Japanese Application No. 2017-164705 filed in Japan on Aug. 29, 2017, the entire contents of which are incorporated herein by this reference.

BACKGROUND OF INVENTION

1. Field of the Invention

The present invention relates to an endoscope in which an image pickup device is disposed in a distal end portion of an insertion section, an image pickup unit configured to convert an object image into an electrical signal, and a method of replacing the image pickup device in the endoscope.

2. Description of the Related Art

An endoscope configured to insert an elongated insertion section into a body of a subject that cannot be observed from outside, to observe the inside of the body using an image pickup device disposed at a distal end portion of the insertion section, and perform a treatment/procedure using a treatment instrument protruding from the distal end portion has been widely used.

The endoscope is expensive. Thus, when the endoscope has failed, the endoscope is repaired by component replacement. An endoscope which has been judged to be defective in an inspection in a manufacturing and assembling process is also reassembled by component replacement.

The image pickup device among components of the endoscope is particularly expensive, and replacement and repair have been strongly desired. The image pickup device includes an optical unit including a distal end lens and an image pickup unit including an image pickup element.

As a disinfection/sterilization method of the endoscope, an autoclave method (high-temperature and high-pressure steam method) is becoming the mainstream. The autoclave method can be immediately used right after sterilization without complicated work, and is low in running cost. However, in the autoclave method, the entire endoscope is exposed to a high-temperature and high-pressure state. Accordingly, the distal end lens in the optical unit is watertightly fixed to a lens frame. An image pickup unit is also firmly fixed to the distal end portion.

Japanese Patent Application Laid-Open Publication No. 2005-227728 discloses an endoscope in which a distal end lens is fixed to a distal end member using an adhesive agent composed of low-melting point glass separately from another optical member in an optical unit held in a lens frame.

SUMMARY OF THE INVENTION

An endoscope according to an embodiment includes a housing including a through hole disposed in a distal end portion of an insertion section, and an image pickup device inserted into the through hole and fixed to the through hole, in which the image pickup device includes an optical unit including a distal end lens and a plurality of optical members, and an image pickup unit configured to convert an object image converged by the optical unit into an electrical signal, the distal end lens is watertightly fixed to a distal end portion of the through hole, the plurality of optical members are held by a lens frame, the lens frame being inserted into the through hole, and a part of the lens frame being bonded to the through hole using an adhesive agent, and the image pickup unit includes a unit frame fixed to the lens frame, a front portion of the unit frame being inserted into the through hole, the front portion being bonded to the through hole using the adhesive agent, and an outer peripheral surface of a rear portion of the unit frame including a plurality of stoppers to which a jig is to be fixed, the rear portion not being inserted into the through hole.

An image pickup unit according to an embodiment is an image pickup unit configured to convert an object image into an electrical signal, the image pickup unit including a unit frame configured to hold an image pickup element inside, in which an outer peripheral surface of the unit frame includes a plurality of stoppers to which a jig is to be fixed.

A method of replacing an image pickup device in an endoscope according to an embodiment is a method of replacing an image pickup device in an endoscope, in which the endoscope includes a housing including a through hole disposed in a distal end portion of an insertion section, and an image pickup device inserted into the through hole and fixed to the through hole, the image pickup device includes an optical unit including a distal end lens and a plurality of optical members and an image pickup unit configured to convert an object image converged by the optical unit into an electrical signal, the distal end lens is watertightly fixed to a distal end portion of the through hole, the plurality of optical members are held by a lens frame, the lens frame being inserted into the through hole, and a part of the lens frame being bonded to the through hole using an adhesive agent, the image pickup unit includes a unit frame fixed to the lens frame, a front portion of the unit frame being inserted into the through hole, the front portion being bonded to the through hole using the adhesive agent, and an outer peripheral surface of a rear portion of the unit frame including a plurality of stoppers, the rear portion not being inserted into the through hole, a jig is fixed to the plurality of stoppers, and the jig is pulled toward a proximal end side of the endoscope so that an image pickup device other than the distal end lens is pulled out of the housing with the distal end portion of the insertion section held.

DETAILED DESCRIPTION OF THE PREFERRED EMBODIMENTS

First Embodiment

Figure 1:
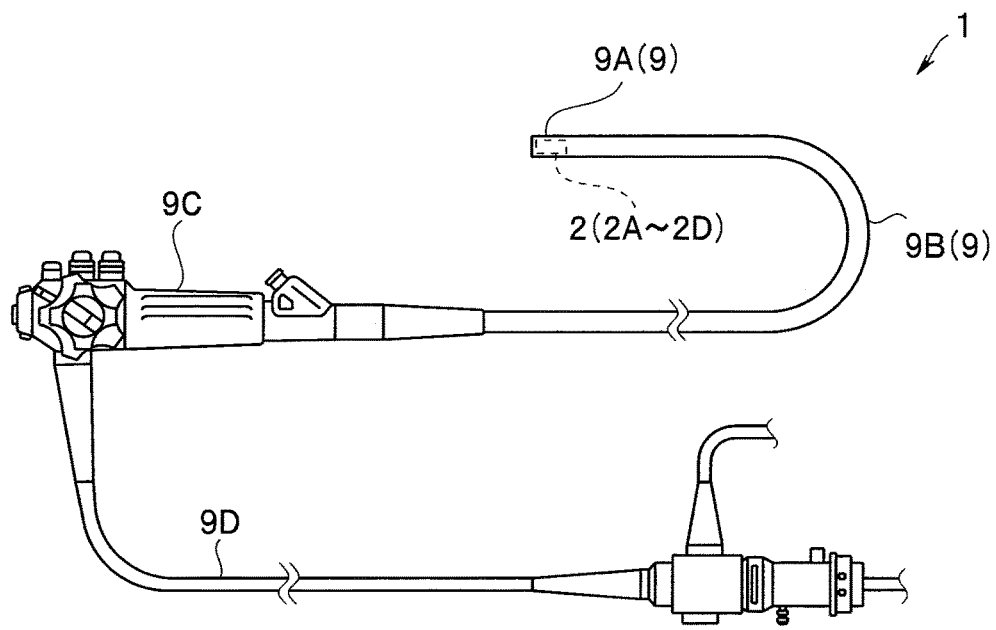
FIG. 1 is an external view of an endoscope according to an embodiment.

As illustrated in FIG. 1, an endoscope 1 according to the present embodiment includes a distal end portion 9A of an insertion section 9 in which an image pickup device 2 is disposed, an operation portion 9C disposed on a proximal end side of an elongated flexible portion 9B of the insertion section 9, and a universal code 9D extending from the operation portion 9C. Note that an image pickup signal outputted from the image pickup device 2 disposed in the distal end portion 9A is transmitted to a processor (not illustrated) via a signal cable 35 (see FIG. 2) into which the insertion section 9 and the universal code 9D are inserted. Note that the endoscope 1 may be for industrial use, although for medical use.

Figure 2:
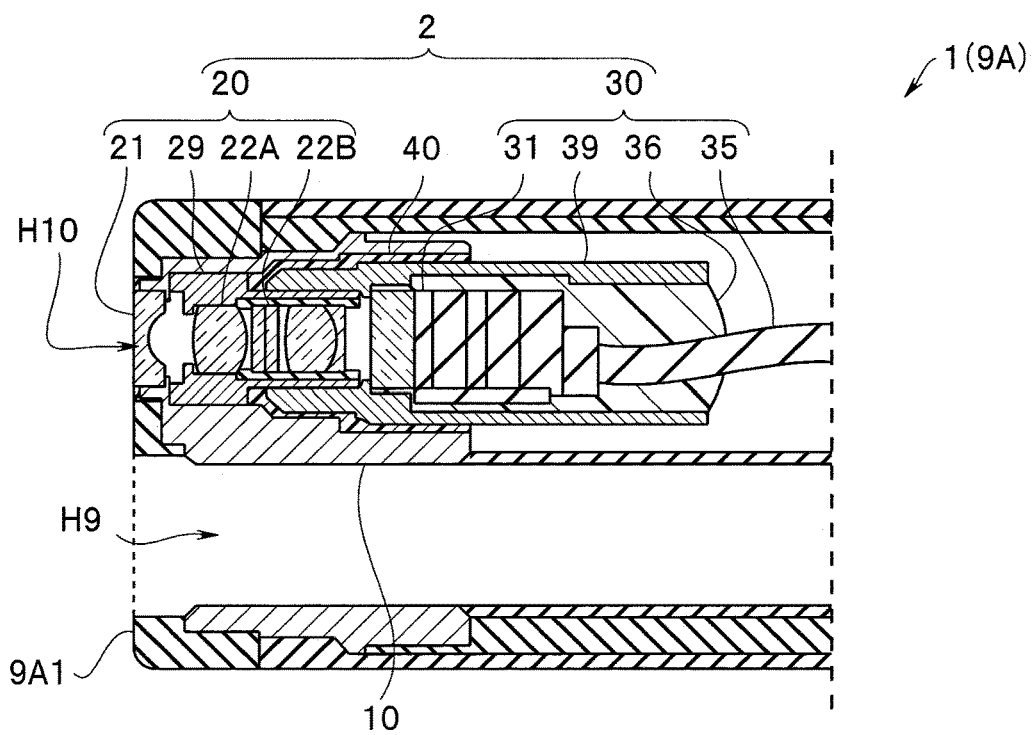
FIG. 2 is a cross-sectional view of a distal end portion of an endoscope according to a first embodiment.
Figure 3:
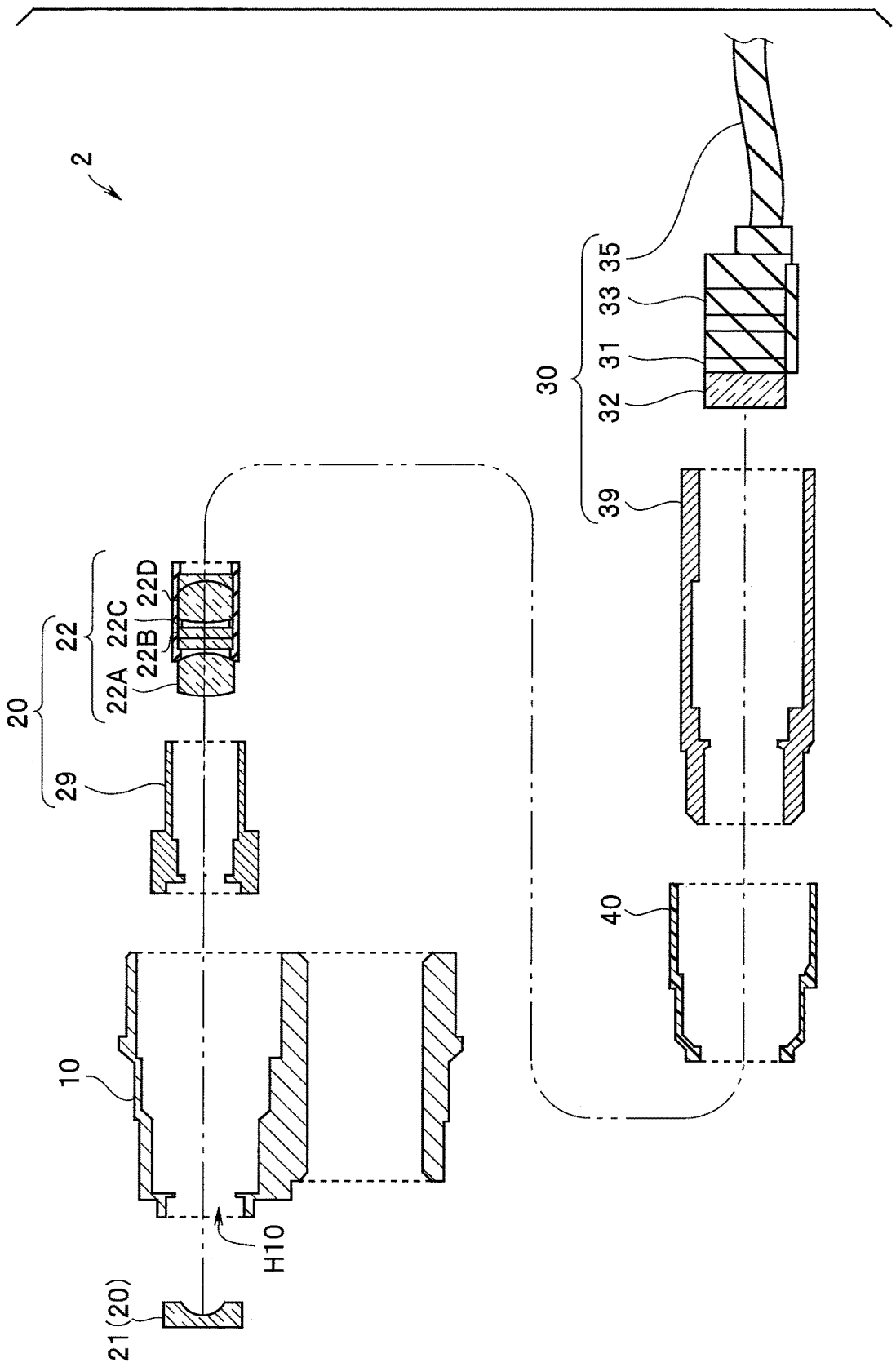
FIG. 3 is a sectional exploded view of the distal end portion of the endoscope according to the first embodiment.

As illustrated in FIGS. 2 and 3, a substantially cylindrical housing 10 is disposed in the distal end portion 9A of the insertion section 9. For example, the housing 10 made of a metal includes through holes H9 and H10. The through hole H9 constitutes an opening portion of a channel into which a treatment tool or the like is inserted. On the other hand, the image pickup device 2 is inserted into and fixed to the through hole H10.

Note that in the following description, it should be noted that drawings based on each of the embodiments are schematic and a relationship between a thickness and a width of each of sections, a ratio of the respective thicknesses of the sections, and the like respectively differ from actual ones, and the sections that differ in dimensional relationship or ratio among the drawings may also be included. Illustration of some of components and assignment of reference numerals may be omitted. Directions of an object, i.e., a leftward direction and a rightward direction in FIG. 2, for example, are respectively referred to as a "forward direction" and a "rearward direction".

The image pickup device 2 includes an optical unit 20 and an image pickup unit 30. The optical unit 20 includes a distal end lens 21 and a plurality of optical members 22 (e.g., a lens 22A, a filter 22B, a spacing adjustment ring 22C, and a lens 22D).

The distal end lens 21 is composed of an optical material such as quartz or sapphire. For the distal end lens 21, a transparent optical material such as stabilized zirconia (YSZ), or yttrium-aluminum-garnet (YAG) can also be used. Amorphous glass having a high autoclave resistance is also applicable to the distal end lens 21.

The distal end lens 21 is a plano-concave lens having a negative power to obtain a wide field of view. However, the distal end lens 21 may be a plano-convex lens depending on a configuration of the optical unit 20. However, an outer surface of the distal end lens 21 is preferably a plane to prevent adhesion and prevent a damage due to impact.

The distal end lens 21 is watertightly fixed to a distal end portion of the through hole H10 in the housing 10. "Watertight" means a state where not only liquid water but also steam is prevented from entering the housing 10 from a gap so that dew condensation may not occur on an inner surface of the distal end lens 21.

The distal end lens 21 inserted into the through hole H10 from a front side (object side) of the through hole H10 is directly fixed to the housing 10 using an adhesive agent, glass, or a solder, for example.

On the other hand, a plurality of optical members 22 other than the distal end lens 21 in the optical unit 20 are inserted into the through hole H10 from a rear side of the through hole H10 with the optical members 22 held in a lens frame 29.

The image pickup unit 30 converts an object image converged by the optical unit 20 into an electrical signal. The image pickup unit 30 includes an image pickup element 31, a cover glass 32, a signal processing unit 33, and a signal cable 35. The image pickup unit 30 is housed in a unit frame 39, and a gap is filled with sealing resin 36.

The lens frame 29 is firmly fixed to the unit frame 39 after a distance from the image pickup element 31 housed in the unit frame 39 has been adjusted. For example, the lens frame 29 and the unit frame 39 are fitted and fixed to each other. A bonding portion between the lens frame 29 and the unit frame 39 may be further reinforced using high elasticity modulus resin such as epoxy or a solder.

The image pickup device 2 inserted into the through hole H10 in the housing 10 from the rear side of the through hole H10 has a rear portion protruding from the through hole H10. In other words, the unit frame 39 has a front portion inserted into the through hole H10, and an outer peripheral surface of the inserted front portion is bonded to the through hole H10 using an adhesive agent 40.

The lens frame 29 is also bonded to the through hole H10 using the adhesive agent 40.

In the endoscope 1, a modulus of elasticity of the adhesive agent 40 with which the image pickup device 2 excluding the distal end lens 21 is bonded to the through hole H10 in the housing 10 is 10 MPa or less.

Figure 4:
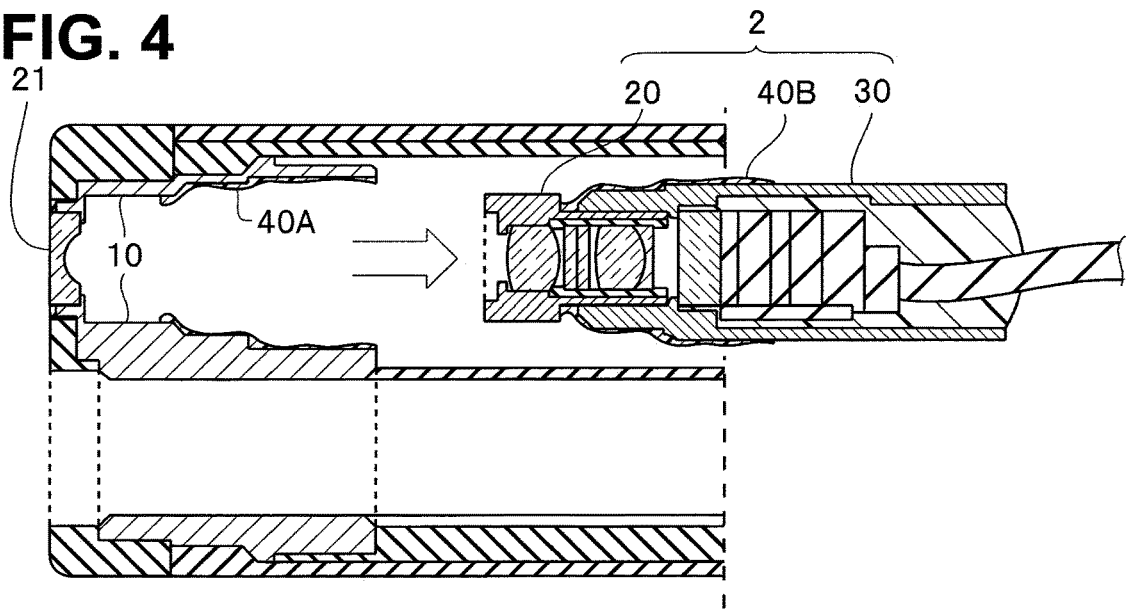
FIG. 4 is a cross-sectional view of a distal end portion for describing a repair process of an image pickup device in the endoscope according to the first embodiment.

As illustrated in FIG. 4, in the endoscope 1, the image pickup device 2 excluding the distal end lens 21 can be easily pulled out backward from the housing 10 when the image pickup device 2 is replaced. In other words, although the housing 10 and the image pickup device 2 are bonded to each other using the adhesive agent 40, the adhesive agent 40 having a modulus of elasticity of 10 MPa or less can be easily fractured by a sheer stress. In other words, the adhesive agent 40 can be easily fractured into an adhesive agent 40A adhering to the housing 10 and an adhesive agent 40B adhering to the image pickup device 2.

When the image pickup device 2 is reused, the adhesive agent 40B adhering to the image pickup device 2 can be easily removed using an organic solvent or the like. Note that the reuse of the image pickup device 2 in the endoscope 1 is strictly reuse of the image pickup device 2 excluding the distal end lens 21.

Even when the image pickup device 2 in which a malfunction has occurred is replaced, the adhesive agent 40A adhering to the housing 10 can be easily removed. Watertight fixing of the distal end lens 21 is complicated because low-melting point glass, a solder, or the like is used. However, in the endoscope 1, the distal end lens 21 fixed to the housing 10 can be used as it is. Thus, replacement work is easier.

As the adhesive agent 40 having a modulus of elasticity (Young's modulus) of 10 MPa or less, flexible silicone resin, flexible polyester resin, flexible polyvinyl chloride resin, rubber, or the like can be used. For example, resin having a modulus of elasticity of 50 MPa cannot be used as the adhesive agent 40 even if the resin is silicone resin. Needless to say, epoxy resin (a modulus of elasticity: 8 GPa) or the like widely used as an adhesive agent is unsuitable for the adhesive agent 40.

Note that a modulus of elasticity (Young's modulus) is a tensile modulus of elasticity measured at a temperature of 25° C. based on a standard (ISO 527-1, JIS K 7161), for example.

A lower limit of the modulus of elasticity of the adhesive agent 40 is 0.1 MPa or more, for example, in an adhesive agent industrially easily available, although not particularly limited.

An adhesive agent 40 composed of significantly soft resin having a modulus of elasticity of 10 MPa or less absorbs vibration of the image pickup device 2 even if a strong impact force is applied from outside to the distal end portion 9A of the insertion section 9. The distal end lens 21 is not integrated with the image pickup device 2 other than the distal end lens 21. Accordingly, the distal end lens 21 in the endoscope 1 is excellent in impact resistance.

Second Embodiment

An endoscope 1A according to a second embodiment is similar to the endoscope 1 and has the same effect as the effect of the endoscope 1, and hence components having the same function are assigned the same reference numeral, to omit description of the components.

Figure 5:
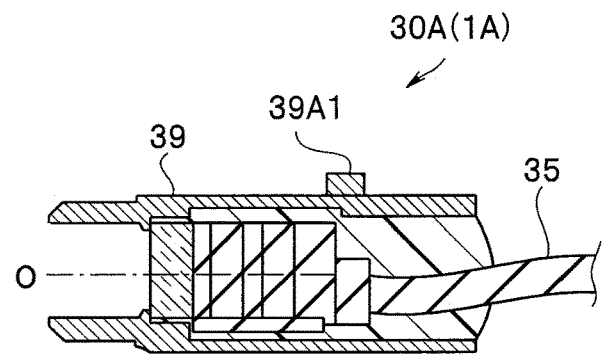
FIG. 5 is a cross-sectional view of an image pickup unit in an endoscope according to a second embodiment.
Figure 6:
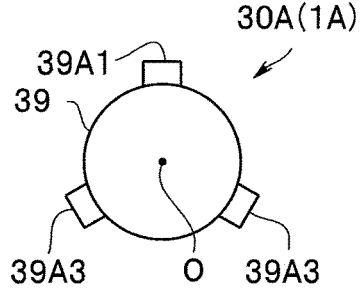
FIG. 6 is a front schematic view of the image pickup unit in the endoscope according to the second embodiment.

As illustrated in FIGS. 5 and 6, in the endoscope 1A, a unit frame 39 in an image pickup unit 30A has a plurality of protrusions (convexities) 39A1, 39A2, and 39A3 as a plurality of stoppers, to which a jig configured to pull out an image pickup device 2 other than a distal end lens 21 is to be fixed, arranged to be rotationally symmetric with respect to a center axis O on an outer peripheral surface of a rear portion of the unit frame not to be inserted into a through hole H10. The image pickup unit 30A includes a unit frame 39 configured to hold an image pickup device 2 inside, and the outer peripheral surface of the unit frame 39 has the plurality of protrusion sections 39A1, 39A2, and 39A3 as a plurality of stoppers to which a jig is fixed. In other words, the outer peripheral surface of the unit frame 39 has the plurality of protrusion sections 39A1, 39A2, and 39A3 to which a jig for pulling the image pickup device 2 out of a housing 10 is to be fixed. The plurality of protrusion sections 39A1, 39A2, and 39A3 may be bonded to the unit frame 39, or may be formed integrally with the unit frame 39. The plurality of protrusion sections 39A1, 39A2, and 39A3 may differ in size.

In work for replacing the image pickup device 2, a signal cable 35 may be disconnected when pulled, for example, to pull the image pickup device 2 out of the housing 10. When an outer periphery of the image pickup device 2 is grasped with a strong force, the image pickup device 2 may be deformed.

In the endoscope 1A, the image pickup device 2 includes the plurality of protrusion sections 39A1, 39A2, and 39A3. Thus, the image pickup device 2 can be easily pulled out of the housing 10 without damaging the signal cable 35 and the image pickup device 2 by using a jig (not illustrated) configured to abut on a front side surface of the protrusion section 39A1 or the like. The stoppers may be respectively a plurality of recesses (concavities) if a jig for pulling the image pickup device 2 out of the housing 10 can be fixed to the recesses. In other words, a method of replacing the image pickup device in the endoscope 1A includes a process for fixing the jig to the plurality of protrusions 39A1, 39A2, and 39A3 and a process for pulling the jig toward a proximal end side of the insertion section 9 with a distal end portion 9A of the insertion section 9 held to pull the image pickup device 2 other than the distal end lens 21 out of the housing 10.

Modification to Second Embodiment

An endoscope 1B in a modification to the second embodiment is similar to the endoscope 1A, and hence components having the same function are assigned the same reference numeral, to omit description of the components.

Figure 7:
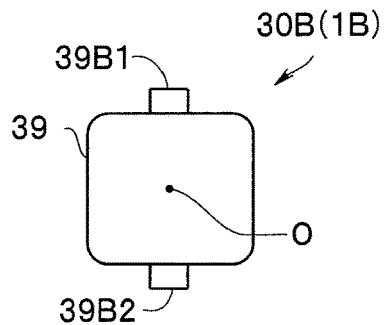
FIG. 7 is a front schematic view of an image pickup unit in an endoscope according to a modification to the second embodiment.

As illustrated in FIG. 7, in the endoscope 1B, an image pickup unit 30B is a substantially rectangular parallelepiped to match an external shape of an image pickup element 31. An optical unit 20 not illustrated has a substantially cylindrical shape, like in the endoscope 1.

The image pickup unit 30B includes two protrusions 39B1 and 39B2 arranged to be rotationally symmetric with respect to a center axis O on an outer peripheral surface of a unit frame 39.

Accordingly, the endoscope 1B has the same effect as the effect of the endoscope 1A.

Third Embodiment

An endoscope 1C according to a third embodiment is similar to the endoscope 1 and has the same effect as the effect of the endoscope 1, and hence components having the same function are assigned the same reference numeral, to omit description of the components.

Figure 8:
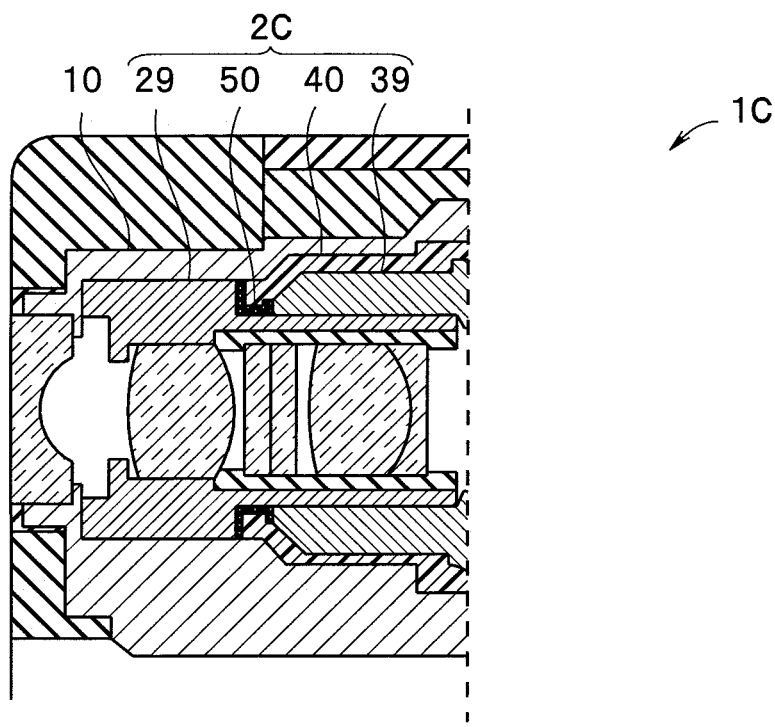
FIG. 8 is a cross-sectional view of a distal end portion of an endoscope according to a third embodiment.

As illustrated in FIG. 8, in the endoscope 1C, an area between a front portion of a unit frame 39 and an adhesive agent 40 and an area between a lens frame 29 and the adhesive agent 40, i.e., a bonding portion between a unit frame 39 and the lens frame 29 is coated with a mold release agent 50. The mold release agent 50 weakens adhesive strength of the adhesive agent 40 to the bonding portion. Note that a region, opposing the bonding portion, in a through hole H10 of a housing 10 may be coated with the mold release agent 50.

As the mold release agent 50, a fluorine-based mold release agent or a silicone-based mold release agent, which is commercially available, for example, is used. The mold release agent 50 may be a liquid or a gel having a high viscosity.

In work for replacing an image pickup device 2C, when the image pickup device 2 is pulled out of the housing 10, the bonding portion between the unit frame 39 and the lens frame 29 may be damaged if a large stress is applied to the bonding portion.

In the endoscope 1C, when the image pickup device 2C is pulled out of the housing 10, a large stress may not be applied to the bonding portion between the unit frame 39 and the lens frame 29.

Modification to Third Embodiment

An endoscope 1D in a modification to the third embodiment is similar to the endoscope 1C, and hence components having the same function are assigned the same reference numeral, to omit description of the components.

Figure 9:
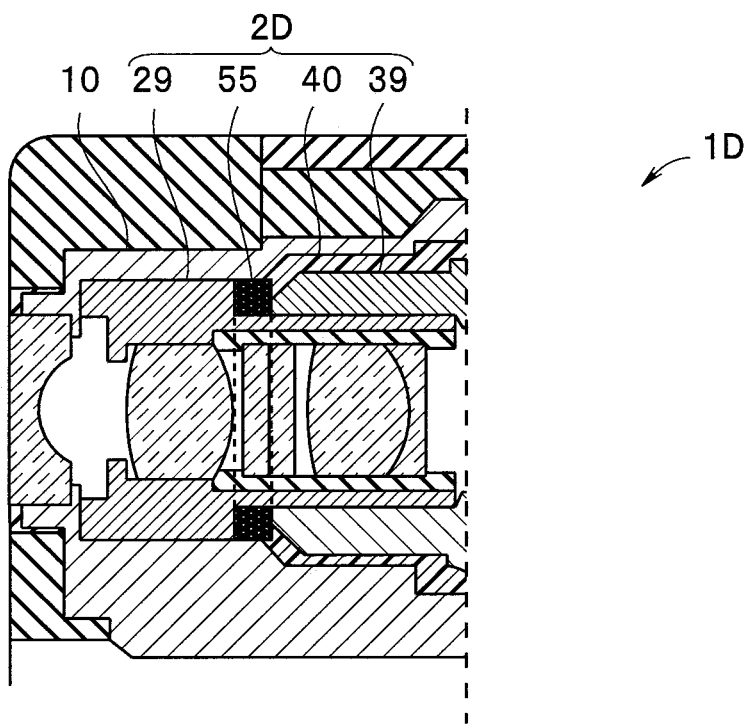
FIG. 9 is a cross-sectional view of a distal end portion of an endoscope according to a modification to the third embodiment.

As illustrated in FIG. 9, in the endoscope 1D, an annular member 55 covering an area between a front portion of a unit frame 39 and an adhesive agent 40 and an area between a lens frame 29 and the adhesive agent 40, i.e., a bonding portion between the unit frame 39 and the lens frame 29 is disposed. For example, the annular member 55 is composed of a silicone rubber tube.

In the endoscope 1D, the bonding portion is not bonded with the adhesive agent 40. In other words, the annular member 55 only covers the bonding portion. Accordingly, in the endoscope 1D, when the image pickup device 2 is pulled out of a housing 10, a large stress may not be applied to the bonding portion between the unit frame 39 and the lens frame 29.

Needless to say, even in the endoscopes 1C and 1D, if the unit frame 39 has a plurality of protrusions arranged to be rotationally symmetric with respect to a center axis on an outer peripheral surface of a rear portion of the unit frame 39, the endoscopes 1C and 1D have the same effect as the effect of the endoscopes 1A and 1B.

The present invention is not limited to the above-described embodiments and modifications, but various changes, combinations, alterations, and the like can be made without departing from the scope and gist of the invention.

The application claims benefit of Japanese Patent Application No. 2017-164705 filed in Japan on Aug. 29, 2017, the entire disclosure content of which is incorporated in the specification and claims by reference.

What is claimed is:

1. An endoscope comprising:
   a housing including a through hole disposed in a distal end portion of an insertion section; and
   an image pickup device inserted into the through hole and fixed to the through hole, wherein
   the image pickup device includes an optical unit including a distal end lens and a plurality of optical members, and an image pickup unit including an image sensor configured to convert an object image converged by the optical unit into an electrical signal,
   the distal end lens is watertightly fixed to a distal end portion of the through hole,
   the plurality of optical members are held by a lens frame, the lens frame being inserted into the through hole, and a part of the lens frame being bonded to the through hole using an adhesive agent, and
   the image pickup unit includes a unit frame fixed to the lens frame, a front portion of the unit frame being inserted into the through hole, the front portion being bonded to the through hole using the adhesive agent, and an outer peripheral surface of a rear portion of the unit frame including a plurality of stoppers projecting from the outer peripheral surface of the rear portion, plurality of stoppers not being inserted into the through hole such that the plurality of stoppers are exposed from the housing and a jig can be fixed to the plurality of stoppers to facilitate removal of the unit frame from the housing.

2. The endoscope according to claim 1, wherein the plurality of stoppers are arranged to be rotationally symmetric with respect to a center axis of the unit frame.

3. The endoscope according to claim 1, wherein an area between the front portion of the unit frame and the adhesive agent and an area between the lens frame and the adhesive agent are coated with a mold release agent.

4. The endoscope according to claim 1, further comprising an annular tube disposed between the front portion of the unit frame and the adhesive agent and an area between the lens frame and the adhesive agent.

5. The endoscope according to claim 1, wherein a modulus of elasticity of the adhesive agent is not less than 0.1 MPa and not more than 10 MPa.

6. A method of replacing an image pickup device in an endoscope, wherein
   the endoscope comprises:
      a housing including a through hole disposed in a distal end portion of an insertion section, and
      an image pickup device inserted into the through hole and fixed to the through hole,
      the image pickup device includes an optical unit including a distal end lens and a plurality of optical members and an image pickup unit including an image sensor configured to convert an object image converged by the optical unit into an electrical signal,
      wherein the distal end lens is watertightly fixed to a distal end portion of the through hole,
      the plurality of optical members are held by a lens frame, the lens frame being inserted into the through hole, and a part of the lens frame being bonded to the through hole using an adhesive agent,
      the image pickup unit includes a unit frame fixed to the lens frame, a front portion of the unit frame being inserted into the through hole, the front portion being bonded to the through hole using the adhesive agent, and an outer peripheral surface of a rear portion of the unit frame including a plurality of stoppers, the rear portion not being inserted into the through hole,
   the method comprises:
      fixing a jig to the plurality of stoppers, and
      pulling the jig toward a proximal end side of the endoscope so that an image pickup device other than the distal end lens is pulled out of the housing while the distal end portion of the insertion section is held.

* * * * *